United States Patent [19]

Lichauer et al.

[11] Patent Number: 5,309,486
[45] Date of Patent: May 3, 1994

[54] NON-CONTACT FLAW DETECTION FOR CYLINDRICAL NUCLEAR FUEL PELLETS

[75] Inventors: John C. Lichauer, Monroeville; Lawrence J. Zana, Hampton Township, Allegheny County; Nicola G. Arlia, Bellevue; John M. Beatty, Murrysville, all of Pa.; Hassan J. Ahmed, Irmo, S.C.

[73] Assignee: Westinghouse Electric Corp., Pittsburgh, Pa.

[21] Appl. No.: 975,050

[22] Filed: Nov. 12, 1992

[51] Int. Cl.$^5$ ............................................. G21C 17/00
[52] U.S. Cl. .................... 376/248; 376/261; 376/258
[58] Field of Search ................ 376/261, 248, 258; 209/528, 538, 564

[56] References Cited

U.S. PATENT DOCUMENTS

| | | | |
|---|---|---|---|
| H1084 | 8/1992 | Bylenok et al. | 73/602 |
| 4,448,680 | 7/1980 | Wills et al. | 209/564 |
| 4,496,056 | 3/1982 | Schoenig, Jr. et al. | 209/539 |
| 4,549,662 | 10/1985 | Schoenig, Jr. et al. | 209/539 |
| 4,821,108 | 4/1989 | Barbagelata et al. | 358/282 |
| 5,147,047 | 9/1992 | Ahmed et al. | 209/538 |
| 5,193,173 | 3/1993 | Seto | 395/425 |

*Primary Examiner*—Donald P. Walsh
*Assistant Examiner*—Meena Chelliah
*Attorney, Agent, or Firm*—Joseph C. Spadacene

[57] ABSTRACT

A non-contact surface flaw detection system for workpieces such as nuclear fuel pellets transports the pellets continuously along an illuminated path while rotating them. A line scan camera records a series of line scans for the pellets and the resulting values of pellet reflectivity are digitized. Pixel values are compared to thresholds defined adaptively by averaging and/or using a video finite impulse response filter, to generate a binary map of "good" and "bad" pixels, that also defines the edges of the pellet in the map. A processor counts and associates bad pixels to logically define and assess blobs of bad pixels. The processor checks for coincidence of the edge pixels with a nominal edge line that best fits the edge, for finding edge flaws. The pellets assessed in this manner are selected or rejected. Camera sensor elements are normalized for gain and offset. Shifting of the pixel data cancels skew produced in scanning moving pellets. Convolution filters cancel isolated bad pixels and enhance contrast at the edge. For processing adjacent areas, the pixel image of the pellets can be tiled, flaws bridging the tile boundaries being assessed as a single blob. The apparatus is preferably arranged for parallel pipeline processing for sidewall and edge defects and can be embodied in a series of modular VME boards.

13 Claims, 9 Drawing Sheets

NON-CONTACT FLAW DETECTION FOR CYLINDRICAL NUCLEAR FUEL PELLETS

BACKGROUND OF THE INVENTION

1. Field of the Invention

The invention relates to the field of automated analysis of workpieces for optically detectable flaws, and in particular to the optical detection and assessment of sidewall and edge flaws in cylindrical nuclear fuel pellets.

2. Prior Art

In the manufacture of nuclear fuel rods, nuclear fuel pellets are formed from a matrix of enriched or natural uranium oxide and are inserted into elongated hollow tubes typically made of an alloy of zirconium, to be used as fuel rods. The pellets are short cylinders and are stacked in the tubes. The tubes are sealed at the ends with end plugs, and pressurized. A plurality of fuel rods are arranged in an array to form the fissionable core of a nuclear reactor.

Defects in the pellets, such as fissures or cracks, can result in chips becoming dislodged from the pellets during reactor operation. Such chips can adversely affect the operation of the reactor. For example, a chip dislodged from a fuel pellet can become lodged within the fuel rod adjacent the interior wall of the rod. The fissionable material in the dislodged chip continues its fission reaction under the influence of nuclear flux in the reactor core. Heat generated at the chip can create a localized area of intense heat on the wall of the fuel rod. This weakens the rod at the point of the chip and may cause a rupture of the rod wall and a leak of high pressure gas from the rod. If this occurs, the reactor may have to be shut down.

Other pellet defects, which may be visible at the surface of the pellets, also can cause adverse effects. For example, the inclusion of metal in the pellet surface may adversely affect the normal fission reaction of the uranium. The pellets must be free of defects such chips, cracks, etc., for optimal operation of the reactor. Conventionally, pellets are inspected visually by human inspectors. Specially dressed inspectors visually examine illuminated trays of lengthwise stacked pellets and manually remove any that are apparently defective. After one side of the pellets is viewed, the trays are covered and flipped over, for viewing the opposite side.

The results of manual inspection of the pellets in this manner are inconsistent due to the subjectivity inherent in human visual inspection. Moreover, manual inspection requires prolonged exposure of the inspectors to the low level radiation produced by the pellets, as well as potential ingestion of dust which the pellets produce. Also, the trays are heavy and physically manipulating them is strenuous and presents a risk of injury.

U.S. patent application Ser. No. 07/640,770, filed Jan. 14, 1991 and entitled Pellet Inspection System, discloses an automated transport arrangement for presenting pellets serially for inspection using an automated viewing apparatus. The disclosure of said Application is hereby fully incorporated. According to the disclosure, the pellets are fed along a conveying means that rotates and axially feeds the pellets as they pass in front of a line scanning camera. The image of the pellets is digitized as a series of sets of discrete digital values representative of axially extending linear portions covering the peripheral surface of each passing pellet. The digital values, which represent the reflectivity of the pellets in a small area or pixel according to a numerical gray scale, are collected and their values are averaged. High and low reflectivity thresholds are defined from the average, and the pixel values are compared to the thresholds thus defined. The number of pixels that fall outside the threshold are counted, and if the number exceeds a predetermined value the respective pellet is rejected. The system is arranged such that the pellets are axially separated from one another as they are fed, whereby it is also possible to use the system to check for proper pellet dimensions without the need to detect the axial ends of the pellet.

Additional examples of optical inspection systems for cylindrical pellets and the like are disclosed in U.S. Pat. Nos. 4,496,056 and 4,549,662—both to Schoenig, Jr. et al, and U.S. Pat. No. 4,448,680—Wills et al.

SUMMARY OF THE INVENTION

It is an object of the invention to provide an optimally effective and convenient image processing system, especially for analyzing data collected in an automated image collection system for nuclear fuel pellets.

It is another object of the invention to adapt general purpose image analysis hardware to the specific needs of nuclear fuel pellet surface flaw detection.

It is also an object of the invention to eliminate problems in known imaging systems relating to the environment of nuclear fuel pellet inspection.

These and other objects are accomplished in a non-contact surface flaw detection system for workpieces such as nuclear fuel pellets that transports the pellets continuously along an illuminated path while rotating them. A line scan camera records a series of line scans for the pellets and the resulting values of pellet reflectivity are digitized. Pixel values are compared to upper and lower thresholds that are defined adaptively, for example pixels within a predetermined range about the average value. In addition, a video finite impulse response filtering process can be applied to reduce noise present in the image. The threshold comparison generates a binary map of "good" and "bad" pixels, the latter being those outside the two thresholds. The binary map also defines the edges of the pellet in the map. A processor counts and associates bad pixels to logically define and assess groups or "blobs" of pixels outside the thresholds. The processor also checks for coincidence of the edge pixels with a nominal edge line that best fits the edge, for finding edge flaws. The pellets assessed in this manner are selected or rejected.

The individual sensor elements of the line scanning camera are tested for gain and offset, and thereafter incoming data from the respective sensor elements is normalized to cancel variations among the sensor elements. Shifting of the pixel data cancels skew produced in scanning moving pellets to enable the image to be processed as an elevation or plan view. Convolution filters are applied to the pixel data and/or to the binary map, to cancel isolated bad pixels and to enhance contrast at the edges of the pellet.

For processing adjacent areas, the pixel image of the pellets can be tiled, or collected in successive subset images that are processed one at a time. Adjacent flaws bridging across the tile boundaries are associated together and assessed as a single blob. The apparatus is preferably arranged for parallel pipeline processing for sidewall and edge defects and can be embodied in a series of modular VME boards.

In discussing image collection and analysis according to the invention, pellet defects are grouped generally into two categories, namely sidebody surface flaws and edge defect flaws. Sidebody surface flaws include, for example, circumferential cracks, longitudinal cracks, connected or branched fissures, thumbnail cracks, pitting and sidebody indications, end capping, circumferential surface chips, unground surfaces, and metal inclusions. Edge defect flaws can be end chips, chatter and the like. This nomenclature is used for convenience in discussing the invention. However, it will be appreciated that the system is useful generally for detecting and selecting for optically detectible attributes of any type.

A wide variety of specific tests may be applied to the pellets to assess quality, and it is possible to be more or less demanding in the selection or rejection of pellets. The invention is described in a manner that permits a range of tests; however only certain exemplary test criteria are specifically discussed as examples. For example, the character of defect found, the size of the defect, its orientation, the number of defects found, the potential relationship of defects, whether the defect is relatively bright or dark, etc., are all potential quality parameters of interest that can be examined.

The invention is also discussed with reference to a preferred embodiment wherein a substantial portion of the image processing steps are arranged as functions of a modular VME board system. Similar processing functions can be embodied using other divisions of hardware and software elements.

BRIEF DESCRIPTION OF THE DRAWINGS

There are shown in the drawings certain embodiments of the invention as presently preferred. It should be understood, however, that the invention is not limited to the precise arrangements and instrumentalities shown, which are intended as exemplary. In the drawings.

DETAILED DESCRIPTION OF THE PREFERRED EMBODIMENTS

Figure 1:
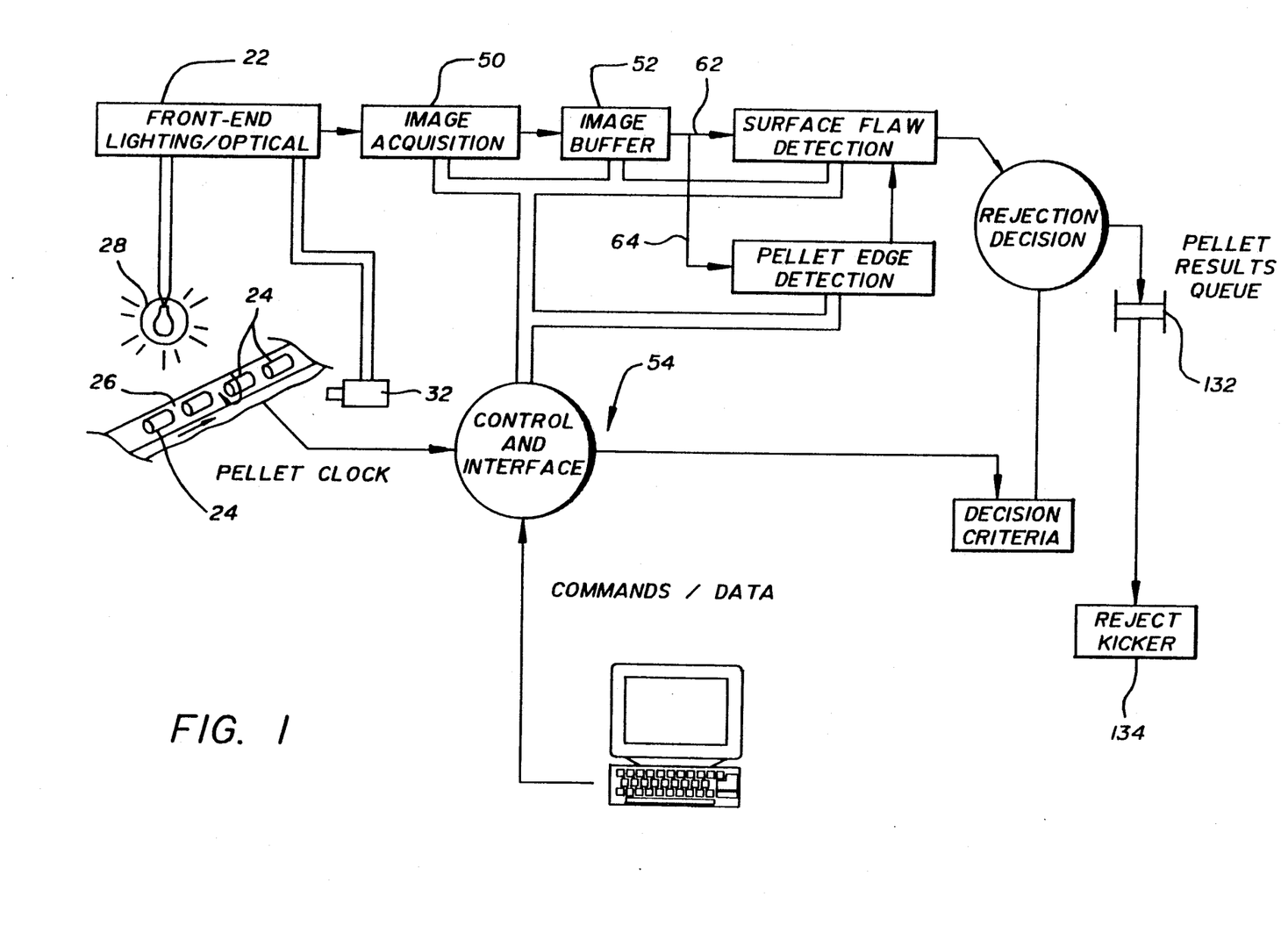
FIG. 1 is schematic block diagram showing the hardware and software functional blocks of a method and apparatus for non-contact surface flaw detection according to the invention.
Figure 2:
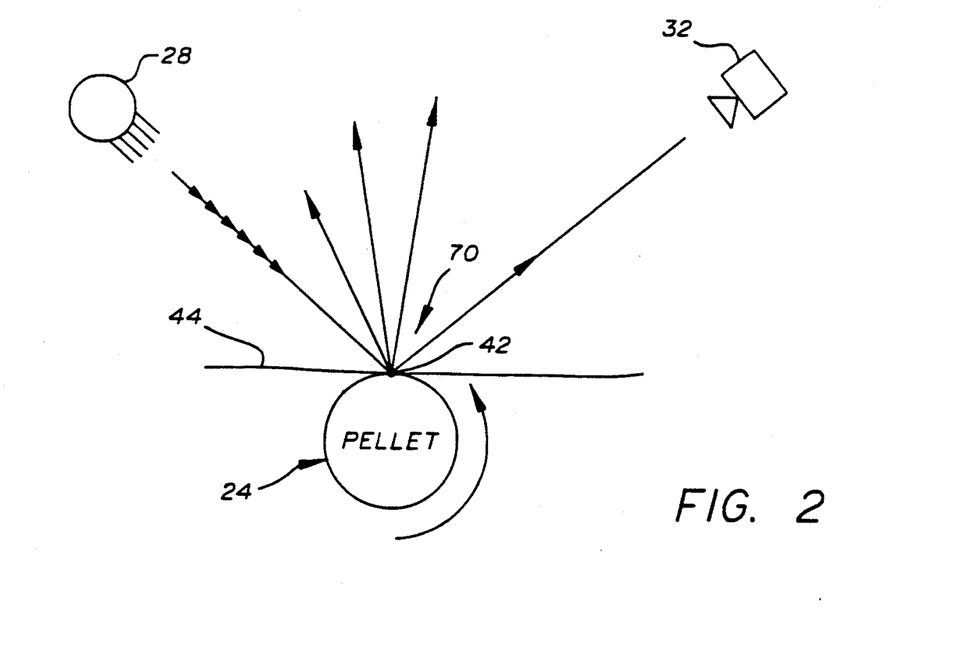
FIG. 2 is a schematic illustration of an illumination and camera means operatively oriented toward a pellet to be examined.

FIG. 1 shows the general hardware and functional elements of a non-contact surface flaw detection system according to the invention. The front-end lighting and optical system 22 acquires images of substantially cylindrical pellets 24 as they are rotated on their axes and translated axially by a material handling system 26, for example as disclosed in U.S. patent application Ser. No. 07/640,770, filed Jan. 14, 1991, which is hereby fully incorporated. The optical system 22 as shown schematically in FIG. 2, comprises an illumination source 28 and a camera 32 mounted to detect changes in the reflectivity of the surface 42 of the pellet 24. Preferably, the illumination source 28 and the camera 32 are mounted at equal angles of incidence relative to a tangent 44 to the pellet at the point being examined, tending to maximize light transmission to the camera 32 when the surface is smooth, and providing good contrast in the event of a crack, chip or similar discontinuity. The reflected light level varies as a function of reflectivity of the surface due to material composition, and due to discontinuities in the surface causing light to scatter as shown in FIG. 2. The discontinuities are thereby detectable as brighter or darker light levels received at the camera.

This arrangement is important to the successful inspection of pellets. The images provided by this optical arrangement provide good contrast between the normal pellet surface and all of the side surface flaws mentioned above, as well as the necessary gray level contrast to detect all of the specified edge defects.

The images from the front-end optical system 22 are digitized by an image acquisition system 50 and stored in an image buffer 52. Upon receiving a "PELLET CLOCK" signal, which can be generated using a photocell pair detecting passage of a pellet or by a proximity sensor, the image processing controller 54 initiates a transfer of the most recently completed pellet image for processing. The image data is processed in both a surface flaw data pipeline 62, which is configured to detect potential sidebody defects, and an edge flaw detection data pipeline 64, which is configured to detect pellet edge boundary defects.

Image acquisition for pellet defect analysis can use commercially available high speed image acquisition hardware, such as the MaxVideo line of modular VME boards marketed by Data Cube, Inc. The camera 32 preferably is a line scan camera such as a Fairchild CAM 1500R or CAM 1830 line scan camera, having a 2,048×1 line of sensor cells. The light source 28 can be a high frequency fluorescent light source such as a fluorescent tube driven by a high frequency (e.g., 60 KHz) driver, such as available from Mercron, thereby enabling several cycles of illumination during each line scan cycle. The sensors in the camera 32 develop a charge as a function of the light level focused on them, and the charges can be shifted serially out of the respective sensors for digitization using an analog to digital converter 66, for numerical analysis and processing.

Figure 3A:
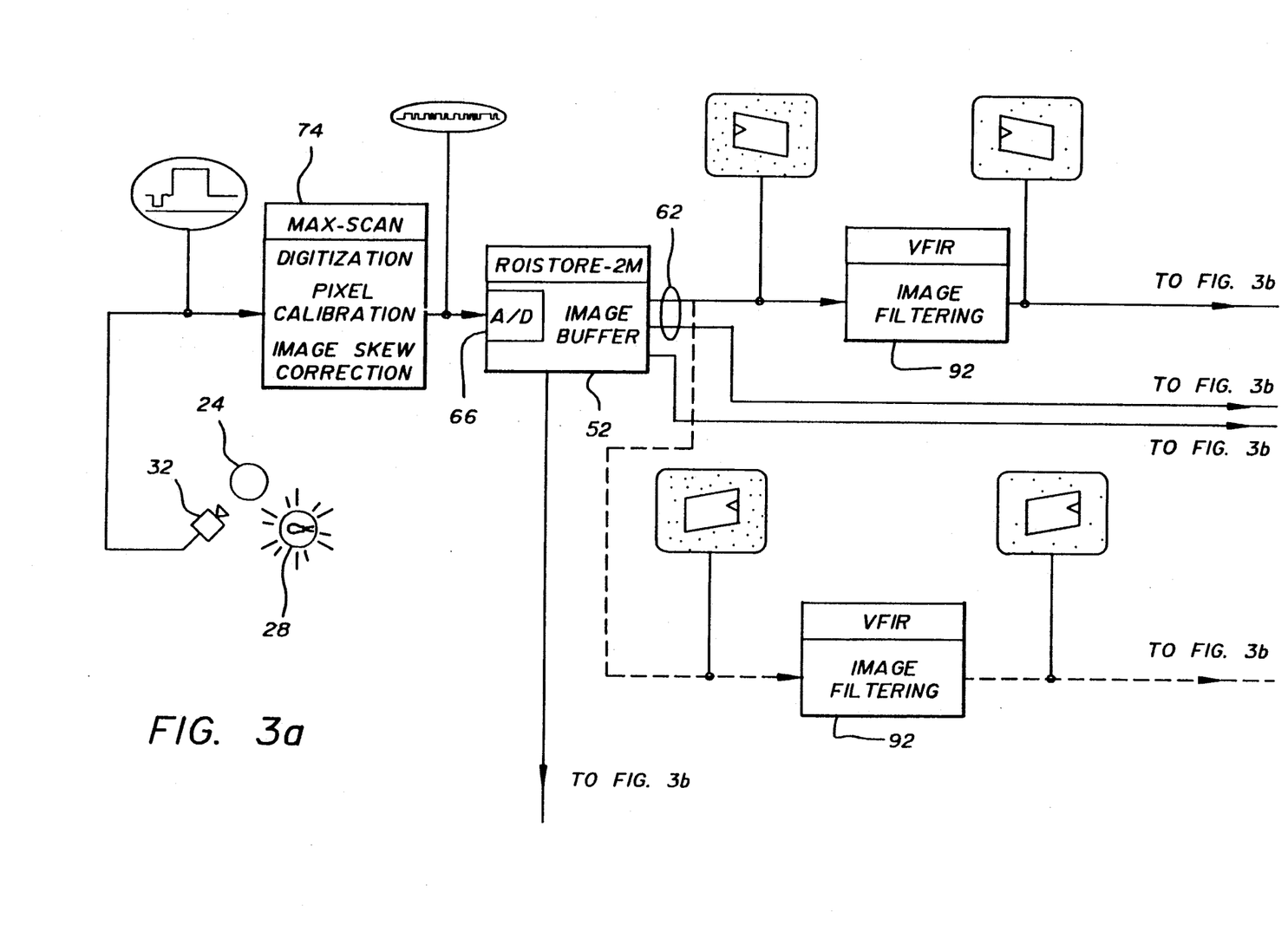
FIGS. 3a-3c are related segments of a schematic illustration of signal processing units in a modular VME data handling system according to the invention, showing the data handling pipelines.
Figure 3B:
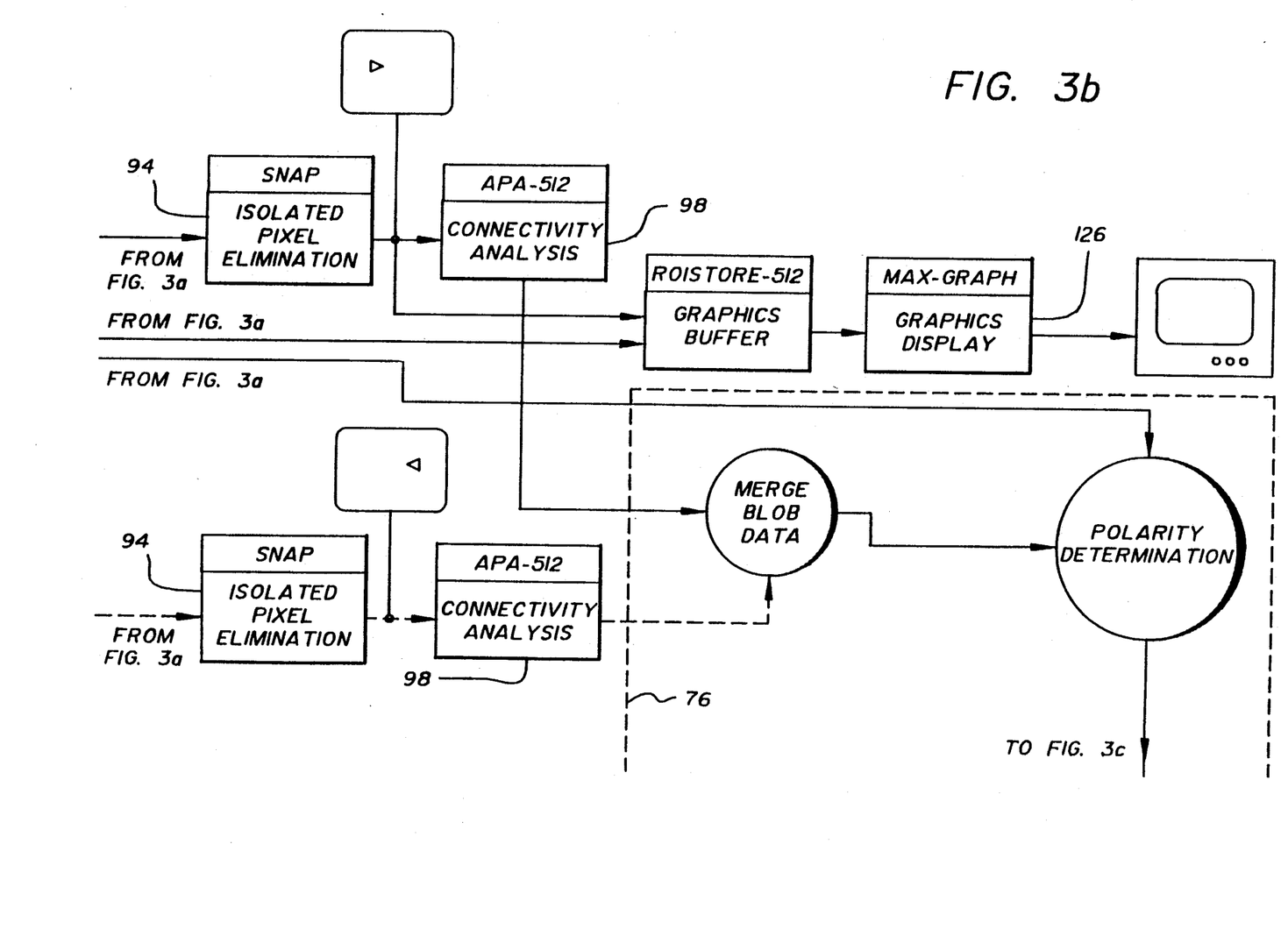
Figure 3C:
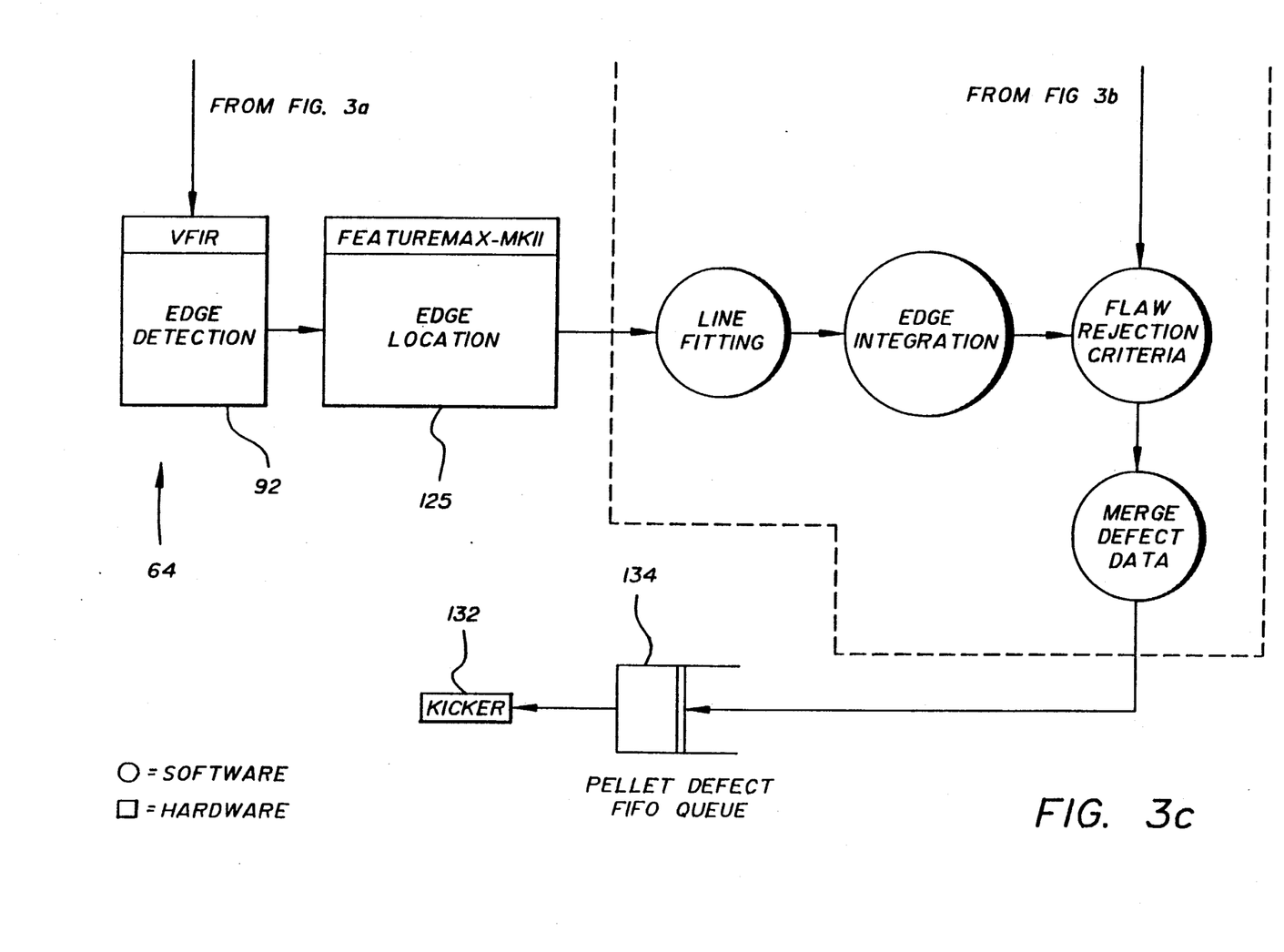

FIGS. 3a-3c illustrate preferred image processing functions in an arrangement wherein the functions are embodied in MaxVideo modules that are coupled to define the image data processing pipelines 62, 64. In general, the boards along the pipelines embody logical and mathematical functions which examine the pellet linescan images for defective areas characterized by reflectivity variations. When processing is complete along the two processing pipelines, potentially defective areas or "blobs" 70 have been identified, and preferably also measured and classified. A processor at the end of the data stream compares the results of the image processing steps to stored information representing the maximum acceptable defect criteria. Pellets 24 characterized by a sufficient number or type of reflectivity variations to be considered defective are flagged for subsequent rejection.

The linescan camera 32 is interfaced to the image processing system through an image processor 74 such as a MAX-SCAN module. This eliminates the need for a linescan camera controller box. Such controller boxes typically are not made for an industrial inspection system as provided according to the invention. A shortcoming of typical linescan controller boxes is that they typically operate at less than the maximum data rate of which the camera is capable. The typical control box, for example, is capable of timing signals that allow a 3 MHz pixel data rate, while the camera may be capable of speeds up to 20 MHz.

Coupling the camera 32 directly to the MAX-SCAN module 74 also allows the system processor 74 or the image acquisition control circuitry 54 to vary operation as may be required, for example to accommodate different pellet transport speeds or the like by varying the pixel data rate. With a camera controller box, important system parameters such as the pixel clock rate and line exposure time must be set manually via knobs on the controller box front panel or the like. Since these parameters are not controlled directly by the image processing system, improper setup could result.

For these reasons, the system according to the invention controls the camera 32 via the MAX-SCAN interface 74 or similar control arrangement having an on board frequency synthesizer. The system thus has the capability of modifying the camera's scan rate and exposure time under system control. The system also can be provided with feedback control loops, for example to operate the camera at timing and exposure levels that ensure the required scanning density and maintain an average pixel level that minimizes the extent to which light and dark pixels may go off scale. If the camera requires or permits parallel processing, for example of the even and odd numbered pixels, the MAX-SCAN form of interface also can sample the two separate data streams coming from the sensor and interleave them into a single coherent image.

The clock signal echoed from the came. a 32 is used to clock an analog to digital (A/D) converter 66 on the MAX-SCAN board. Using the camera's clock compensates for any delay introduced by cable length (because the clock signal travels the same length as the data signal). This allows the pixel clock used by the A/D to remain in phase with the data, and also allows high frequency operation. Shielded twisted pair cabling and differential driver circuits are preferred for optimal noise immunity.

The MAX-SCAN module 74 converts the analog signal levels generated by the CCD elements of the camera 32 to digital numeric data. More particularly, the MAX-SCAN interface module 74 produces digital data that is compatible with the system bus, i.e., a MAXbus compatible digital signal.

The interface module (MAX-SCAN) 74 also provides for pixel-by-pixel gain and offset compensation. Gain and offset compensation on a pixel-by-pixel level is extremely useful in surface inspection of nuclear fuel pellets and the like, allowing an increase in sensitivity of the system by compensating for photo response non-uniformities among the sensor elements or due to system optics. Diffuse reflectance standards in the optical arrangement allow calibration for each individual pixel of the linescan camera 32 (off-line). The pixel performance and the specific character and setup of the illumination source 28 and optics are thereby normalized for all the pixels of the camera sensor, compensating for photo response non-uniformities. Once calibration is performed, the resulting gain/offset data, as loaded into the digitization hardware (MAX-SCAN), allows individual pixel corrections to be accomplished in real-time during subsequent on-line system operation.

The sensor calibration procedure gives the system the ability to compensate for the inherent non-uniformities in the front-end optical sensor system, the net result being a very uniform image field, independent of any radiometric perturbations caused by the lighting, optics, or sensor element variations.

Preferably, the pellets 24 are scanned while rotating and in linear motion. The invention provides a unique solution to the image skew problem encountered in line scanning of the moving pellets. If the pellets were held stationary in front of the camera 32 and rotated without any forward motion, image skew would not occur. However advance of the pellet in the time between scans must be taken into account if the data is to be mapped directly into an elevation-type X-Y memory array of the pixel image.

Figure 4:
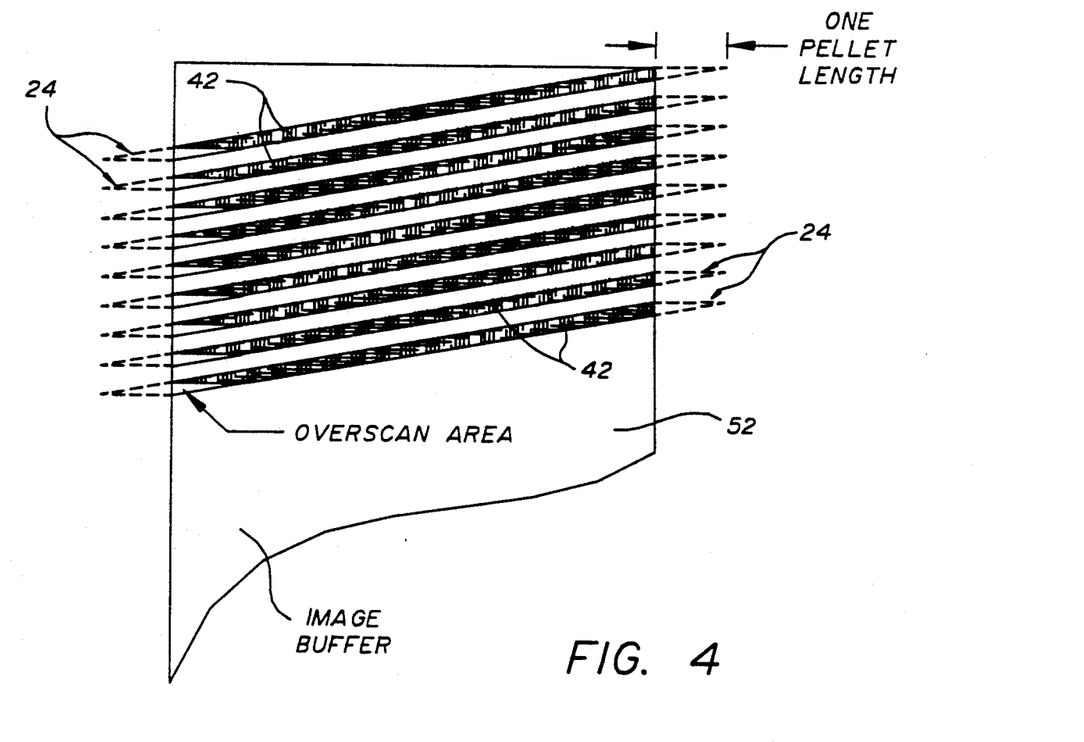
FIG. 4 is a diagrammatic illustration showing skewing of linescan data in an image buffer due to linear motion of the pellet.
Figure 5:
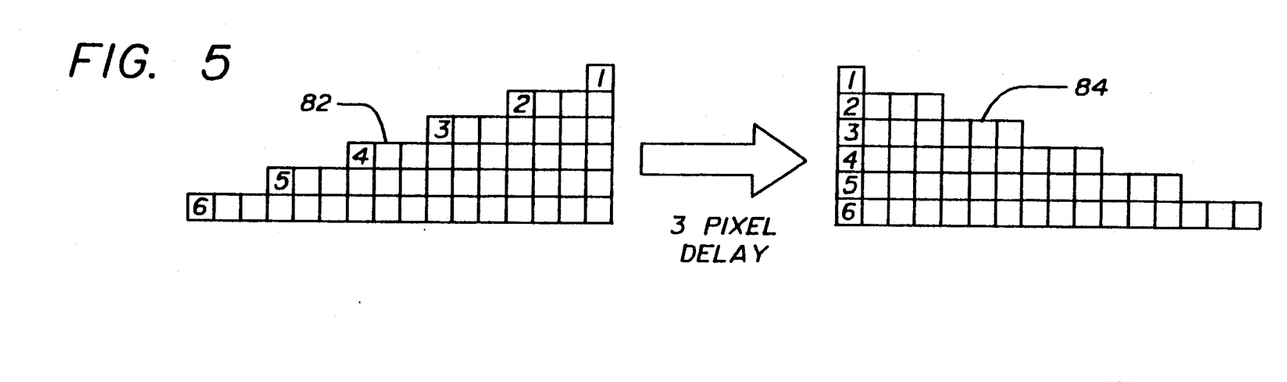
FIG. 5 is a diagrammatic illustration demonstrating correction of the skewing shown in FIG. 4 by introducing a plural-pixel delay.

FIG. 4 illustrates how successive images of moving pellets 24 normally map to the data in the image buffer 52. As a pellet enters the horizontal field-of-view of the line scan camera 32, e.g., moving from right to left in FIG. 4, the first row of pixels to contain reflectivity data on a given pellet will contain only a limited number of pellet pixels (e.g., one or two) along the right hand edge of the row. When the next line of pixels is acquired from the camera (for example about 1 msec later), the pellet 24 has moved to the left by an amount determined by the rate of linear advance of the pellets, for example by 7.5 mils. Therefore, in the next row three more pixels contain data on the pellet than in the previous row. Moreover, the pixels for the successive rows are misaligned with the previous row. On encountering the leading edge of the pellet, the increase in the number of active pixels continues until the pellet is completely within the camera's field-of-view, at which time each successive row contains the same number of pixels, but each row is shifted left three pixel positions on the pellet relative to the previous row's pixels. In FIG. 5, the result is a leading series of pixels 82 that is skewed. As the pellet leaves the field-of-view, the number of pixels in each row containing pellet data likewise decreases by three, until the pellet is completely out of the field-of-view.

The signal processing architecture of the preferred MaxVideo system is characterized by circuits such as gating and the like, designed to process rectangular sub-regions of the image buffer, i.e., tabular or aligned X-Y memory locations. However with reference to FIG. 4, a rectangular sub-region of successive locations does not completely contain one and only one pellet image. According to the invention, the image buffer 52 is made effectively to output each successive row by a displaced number of pixels relative to the previous row. For example, assuming the pellet is transported from left to right relative to the camera, each row is shifted right by a number of pixel spaces relative to the previous row that is a function of the transport speed. This shift causes the successive pellet line images to align in the stored data, justified to the last pellet pixel in the row and to the edge of the pellet. The conversion to the skew-corrected image 84 in FIG. 5 enables simple processing of the image in the successive processing modules as if the entire X-Y array of pellet surface data had been captured at once.

The right shift, e.g., of three pixels as shown in FIG. 5, can be accomplished by causing the MaxVideo image buffer (MEGASTORE) 52 to count three more pixels in each row than were actually collected. The image buffer 52 operates logically by justifying the data to one side of the sensor elements defining the pixel collection means; however the image of the moving pellet progresses, and this is corrected according to the invention. Each successive row of data is then output to downstream processing modules, three pixels to the right of the previous row as shown in FIG. 5, for processing in a manner that allows spatial convolution masks and the like to be applied over X-Y subregions of memory locations in a straightforward manner. This relatively simple correction implements a first-order correction of the pellet's alignment and enables use of X-Y image processing modules such as the Max Video modules in a manner that would not otherwise be possible.

The problem remains to locate the pellet data in the image buffer 52 and to define a region of interest (ROI) that totally contains the pellet to be processed (and no other pellets). By knowing the relevant parameters of pellet spacing, rate of advance and camera line scanning frequency, it is possible to predict nominally where in the image buffer 52 the next pellet to be processed should be stored, relative to the location of the most recent pellet processed. The pellet clock also provides a form of synchronization. Predicting the location of the pellet image in the buffer 52 is used to narrow the search region so that a binary search can very quickly define the pellet ROI.

Preferably, a number of pellet images are in process at any one time. On each pellet clock signal, the system updates the predicted storage location for each of the five pellets being tracked in the image buffer at that time. As each pellet proceeds through the field-of-view, the ROI that completely encloses that pellet is updated on each pellet clock (133 msec at 7.5 pellets per second), so that when the pellet leaves the field-of-view, a ROI transfer is immediately initiated to begin the processing cycle for that pellet.

Figure 6:
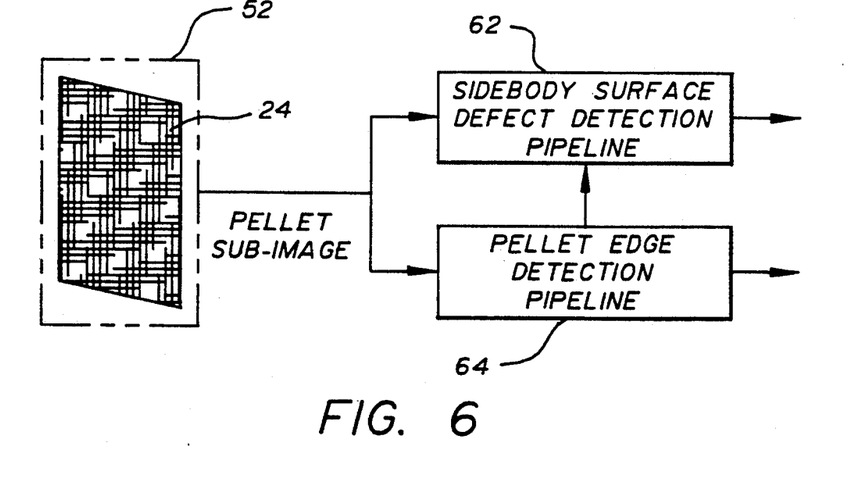
FIG. 6 is a functional block diagram showing the separate data processing pipelines according to the invention for sidebody defect detection and edge defect detection.

Having captured, aligned and located pixel data for a pellet, the flaw detection functional elements analyze the data for variations in surface reflectivity. The flaw detection elements receive sub-images of individual pellets from the image buffer defining regions of interest, and detects in the pixel data pattern localized regions of potential flaws on the pellet surfaces as represented by variations in reflectivity. Such localized potential flaws, which typically are represented in successive line scans, generally may be termed "blobs," and include such physical characteristics as cracks which may be aligned in any direction, end capping, connected or unconnected cracks, pits or voids, metal inclusions, variations in edge or surface smoothness and the like. The blobs 70 are identified and processed along image processing pipelines 62, 64 as shown in FIG. 6.

Data from the pellet edge detection pipeline 64 is used by the surface flaw pipeline 62 to locate potential sidebody and edge defects. Blob data representing aspects of potentially rejectable defects is assimilated from the pipelines and passed on to the flaw rejection section, which performs defect determination and discrimination as explained more fully hereinafter. Preferably, flaw detection involves two separate processing pipelines, one detecting the characteristics of surface flaws, the other detecting the characteristics of pellet edges.

The pellet sub-image or region as received from the image buffer completely contains a single pellet image. Therefore, any sidebody surface flaws occurring within this sub-image belong to a known pellet. A buffer in the MEGASTORE module is used to convert the sub-image from a ROI format to a standard RS-170 format. This is desirable to enable use of the Max Video APA-512 boards, which support RS-170. A video finite impulse response (VFIR) module 92, which performs a low-pass filter operation on the spatial distribution of pixels, filters the sub-image to remove noise without substantially degrading the image itself, thereby improving the signal-to-noise ratio.

Figure 7:
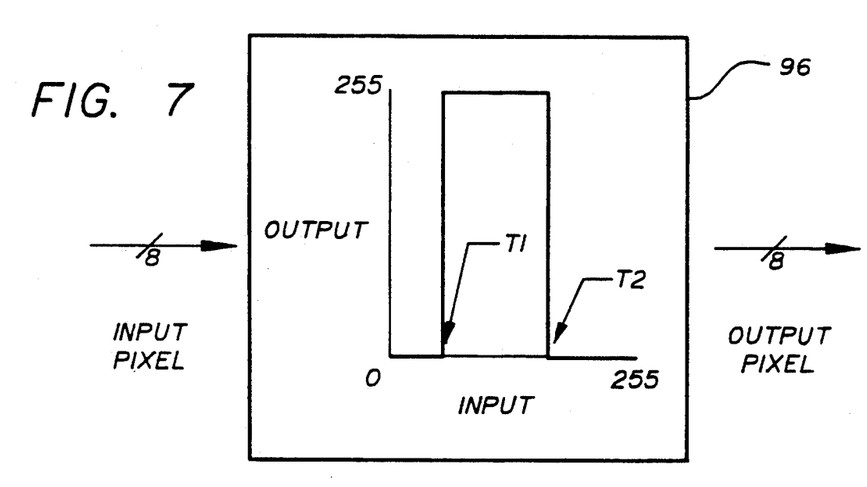
FIG. 7 is a graph showing application of pixel gray scale data to a dual threshold.

A Max Video SNAP module 94 is coupled into the data stream downstream of the VFIR filter 92. The SNAP module 94 implements a dual threshold function using its lookup table, as shown in FIG. 7. Any input pixel with a value between the two thresholds T1 and T2 is output as one value (e.g., 255). Any input pixel values less than T1 or greater than T2 (or equal to such thresholds) are output as a different value (e.g., zero). The specific values of the thresholds can be set at a predetermined value above and below the average "good" pixel value, which is learned over time. These out-of-threshold pixels are of interest because they potentially belong to or border a flaw 70 or reside in the background (i.e., off the pellet in the image collected by the camera 32).

To account for gradual surface reflectivity variations, an adaptive threshold defining technique makes use of the mean gray values for the normal pellet surface, which is accumulated by sampling the MEGASTORE image memory 52. (An alternate solution is to use a FEATUREMAX-MKII module if more speed is required). Preferably, the adaptive threshold technique includes a learning factor relating to one or both of the complete pellet surface and the cluster or area of pixels adjacent the area being examined. On each cycle, the threshold, T, can be updated according to the mean value of the normal pellet surface $\mu_K$ as follows:

$$\epsilon_K = (\mu_K - M_{K-1})$$

$$T_{K-1} = T_K + \rho^* \epsilon_K$$

$$M_K = M_{K-1} + \tfrac{1}{2}\alpha^* \epsilon_K$$

where $M_K$ is the nominal mean of the good pellet surface pixels, $\rho$ is the learning acceleration factor ($\rho << 1.0$), and $\alpha$ is the cluster mean learning factor.

Figure 8:
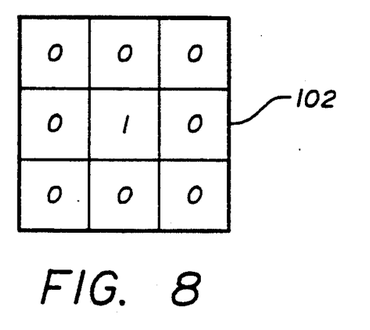
FIG. 8 is a table showing a convolution mask applied to the pixel data for removing apparent defects represented by isolated single pixels.

A predetermined minimal defect criteria is preferably defined for side-body flaws. Any isolated flaw that is smaller than this minimum pixel size is considered not of interest. An exemplary minimum flaw size is 6 mils × 15 mils, which translates to a pixel size of 2.4 × 6 pixels. In order to avoid overwhelming the downstream APA-512 image processor module 98 with single pixel blobs, the SNAP module 94 can eliminate isolated out-of-threshold pixels from consideration by applying a convolution mask to the data. For example, the SNAP module can successively check the relationships of pixels within a 3 × 3 neighborhood, on a pixel by pixel basis to identify and cancel isolated pixel flaws such as single pixel blobs. The SNAP mask 102 for this purpose, as shown in FIG. 8, defines a relationship of a single "1" (flaw) pixel, surrounded on all eight possible sides by "0" (good) pixels. SNAP module 94 outputs a "0" pixel to replace an isolated "1" whenever the relationship of pixels in a local 3 × 3 neighborhood matches the mask. Thus, isolated flaw pixels are eliminated from the image stream.

The image data processing as described to this point separates flaw pixels from good pixels, and for the remainder of the side-body surface flaw pipeline 62, the "good" pixels are no longer of interest. Since both the good pixels (with a value of 255) and the flaw pixels (with a value of 0) are passed on to the APA-512 image processor module 98 with the image data, an additional threshold within the APA-512 can used to separate them so that only the patterns of the bad pixels need to be stored for further analysis, which effectively compresses the data and speeds processing.

The APA-512 image processor module 98 accepts the input sub-image (which has already been effectively separated into "good" and flaw pixels by the SNAP module), and implements a connectivity analysis function to determine whether flaw pixels should be associated together as aspects of a larger defect, and if so to assess the defect. The APA-512 outputs a number representing a count of the blobs 70 and their associated seed parameters (which define characteristics of interest in defining the flaw and in making the decision of whether to reject the pellet). The output describes the corresponding blob 70 in a manner that allows the system to distinguish between larger or more numerous defects, smaller or less numerous defects, and types of defects. It is thus possible to accurately select pellets of higher quality.

Figure 9:
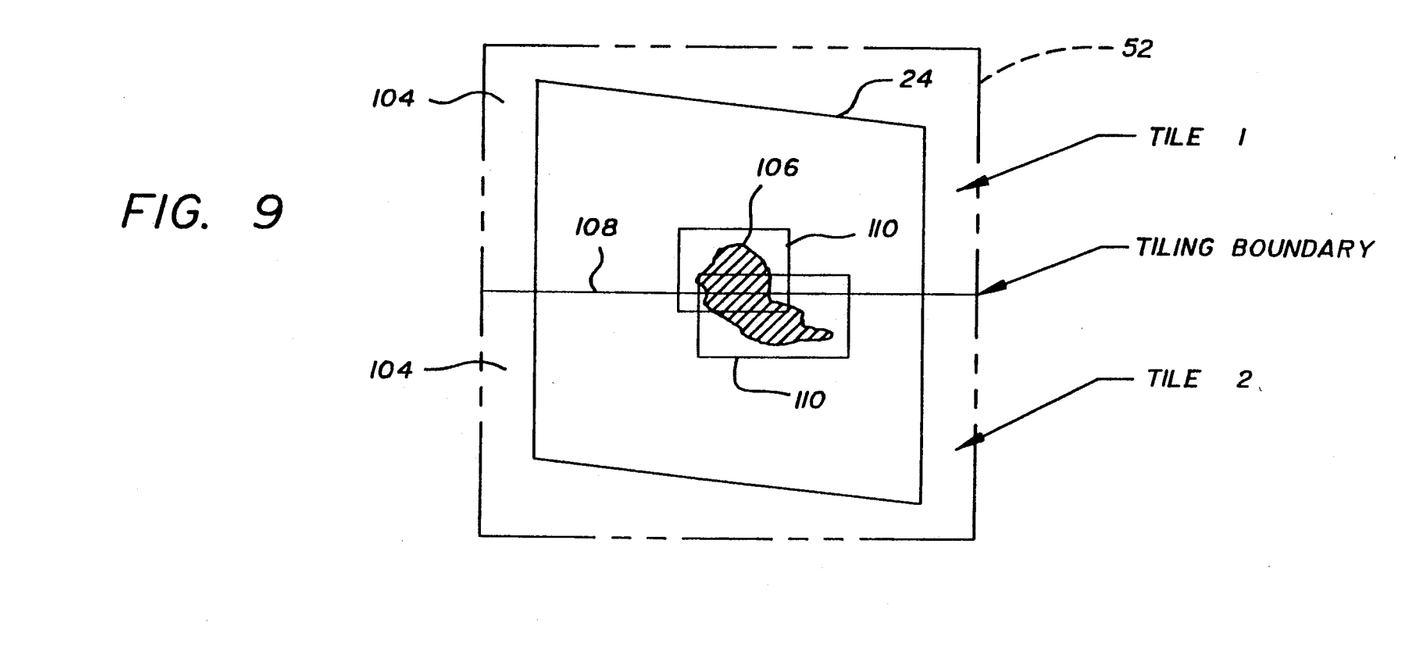
FIG. 9 is an illustration of tiling of a pixel array for identifying blob defects that may extend across the border between adjacent tiles.

Depending on the optics and the size of the object being inspected, the image size may be greater than the maximum allowed by the image processing board, such as the MaxVideo APA-512 board 98. If this is the case, the image is processed tile by tile until processing of the full image is complete. In the case of pellet inspection, only two tiles typically are required to completely cover the surface of the largest pellet, including overscan. Any flaws within each tile will generate blob seed parameters as usual. To handle the case of flaws that cross the boundary between adjacent tiles as shown in FIG. 9, a check is made for a corresponding blob 106 in the adjacent tile 104 when a blob 70 is found in a first tile adjacent the boundary 108 between the tiles. If both tiles contain a blob at or near the boundary, the blob seed parameters for the two tiles 104 are considered in combination, thereby merging the two blobs to define a larger blob and/or a blob with characteristics generated from the images from both tiles.

For potentially related blobs in adjacent tiles, a bounding box procedure limits examination of the adjacent tile for blobs to a predetermined distance from the boundary. By comparing the two flaw bounding boxes 110 of the adjacent blobs and tiles, a quick check is made as to whether or not the two blobs connect across the boundary 108 (i.e., whether the bounding boxes overlap). If so, they are combined. If not, they simply are counted as individual blobs 70. If there is a question as to overlap, the routine can test boundary pixel values and/or flaw pixel locations to determine if the blobs truly connect. If they do, the blob parameters are merged, and a single (large) blob is found and passed on to the routines provided for making the accept/reject decision. Otherwise, the two are processed as individual (smaller) blobs. The tiling procedure easily accommodates flaws that cross the tiling boundary, and merges them where appropriate. Of course, both the occurrence of a relatively larger blob and the occurrence of more numerous blobs reflect adversely on the pellet 24, and either may be sufficient in a particular instance to cause a rejection decision.

The end result of the surface processing pipeline 62 as described is a list of blobs and associated seed parameters describing the blob, each one potentially representing a defect along the side body of the pellet. With the exception of the merging of blobs located on the tile borders, all of the described processing can be implemented in hardware and operated at a high data rate. For example, gating arrays readily can implement the SNAP mask according to FIG. 8 or the like, whereby the required outputs are generated while simply shifting the pixel data through memory registers.

A pipeline 64 is also provided for pellet edge detection processing. The image as received from the image buffer 52 by the edge defect pipeline completely contains an image of the pellet. Therefore, any edge defects located within this image belong to a known pellet.

Figure 10:
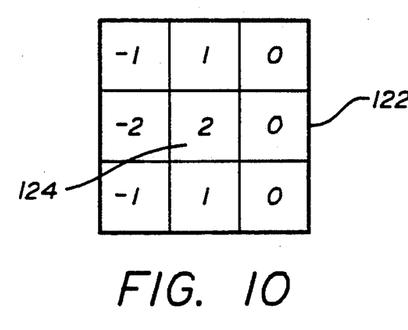
FIG. 10 is a table showing a convolution mask applied to the pixel data for emphasizing contrast defining edges of the pellet being examined.

The first step in this pipeline is to define a nominal edge of the pellet. This is accomplished by using a video finite impulse response filter (VFIR) 92 and another convolution mask. In this case the convolution mask contains weighting factors designed to enhance pixels that lie on a vertical edge gradient. FIG. 10 shows an appropriate mask 122 for emphasizing the vertical edge, i.e., enhancing the contrast at the edge by producing a larger absolute value or output at vertical edges than at other features, such as horizontal edges. Since the edge detection function processes numerical grayscale data, it has a higher tolerance for variations in average gray level value than a binary system as used for isolated flaw pixels and in the threshold definition steps according to the surface data pipeline. It also improves the sub-pixel resolution accuracy of the linear regression function to follow.

The convolution mask of FIGS. 10 is three by three pixels (as was that of FIG. 8). It is also possible to have convolution masks of other sizes. The convolution output for a given pixel according to FIG. 10 is produced by multiplying the factors at each position in the convolution mask box, with the value of the pixel having the corresponding spatial relationship to the center pixel 124, as defined by the mask box, and then adding the sums. The convolution mask factors are weighting factors that favor an aspect which is to be found in the image, such as the vertical edge in FIG. 10. It is also possible to define convolution masks that favor other patterns of pixels, such as a hole of a predetermined size, a vertical or horizontal crack, etc. By applying such convolution masks to the pixel data, the feature favored by the mask is enhanced in the pixel data and is more readily found, measured and otherwise processed.

The edge detection pipeline preferably uses a FEATUREMAX-MKII module 125. Upon detecting a vertical edge, the FEATUREMAX-MKII module 125 extracts the X/Y coordinates of the left and right edge pixels. Each coordinate is tagged appropriately, according to whether or not it came from the left edge (and has a strong positive value following the enhancement via convolution according to FIG. 10), or the right edge (which has a strong negative value).

Once the coordinates of the pellet edge are available, a second order correction may be desirable to correct for image skew. This is desirable if the first order correction assumed a constant linear translation speed, and minor variation in linear speed occurs. A single pixel error can result from as little as 0.1% variation in translation speed, causing a spatially periodic disturbance in the pellet edge locations. There is also a potential error of ±1 pixel position due to digitization. If, on a given row, both the left and right edges are displaced in the same direction and by the same amount, and the difference between the two edges corresponds to the expected pellet length, then the displacement can be corrected for that row. Thus the rows are aligned as a processing step prior to examining them for defects.

The corrected coordinates of the left edge pixels are input to a linear regression routine to determine the nominal line in the image space that best describes the left edge of the pellet, normally a straight line. The process is repeated for the right edge pixel coordinates. The edge lines isolate the background pixels from the pellet surface pixels. Any edge defects can be detected in essentially the same manner as surface sidebody flaws, i.e., by finding and associating areas or blobs 70 which depart from nominal characteristics.

An alternate method of processing for edge flaws is to use the foregoing edge lines to update a mask generated by a MAX-GRAPH module 126. This mask can be binary, and functionally describes where in the image memory the outermost pellet pixels of an ideal pellet would reside along each edge of the pellet 24 (as defined by the best-fit edge lines). It is then a simple matter to determine on a pixel-by-pixel basis if the edge pixels actually found are along the smooth ideal edge lines, or are displaced outwardly or inwardly by one or more pixel positions. The number of displaced edge pixels and the parameters of blobs of associated displaced edge pixels are determined for assessing edge defects.

An arithmetic logic unit (ALU) such as contained in the MAX-SP module preferably is used in a logical-AND mode to compare the two binary sub-images, one sub-image representing where pellet pixels are ideally expected, and the other indicating where pellet pixels actually are found in the particular pellet. The output of this operation is a logical "1" for each pixel that was found in the desired locatio.., and a logical "0" for each pixel where a pellet pixel was supposed to be found but was not found. The logical "0" pixels are, by definition, edge defect pixels. The FEATUREMAX-MKII module 125 can be used to count the edge defect pixels and the number of edge defect pixels is passed on to be factored into the accept/reject decision.

The flaw rejection function is based on the blob data on potential surface and edge pellet defects from the flaw detection sections. The flaw rejection processor converts blob seed parameters to defect parameters, compares the defect parameters to user programmable rejection criteria such as the size, type and number of defects, etc., and generates an accept/reject decision for the pellet. This decision, along with supporting defect parameter data, is placed into a first-in-first-out (FIFO) queue 132 or shift register that is synchronized with the transport of the pellets. A "REJECTION ENABLE" signal is shifted through the FIFO 132 along with the advance of the corresponding rejected pellets, and activates a reject mechanism 134 at the appropriate time to reject a defective pellet, e.g., by diverting the pellet from the stream of accepted pellets.

For each potential defect (PD), blob seed parameters and computed parameters are compared against predetermined rejection criteria, which preferably is programmable. As shown in Table I, the number, character, dimensions and relationships of defects are factored into the accept/reject decision. Any blob or plurality of blobs that meets the predetermined criteria is tagged as a defect, and the pellet description structure is updated with that defect information. Any given pellet 24 can conceivably have more than one defect, or the specific defects found can be more or less serious.

Figure 11A:
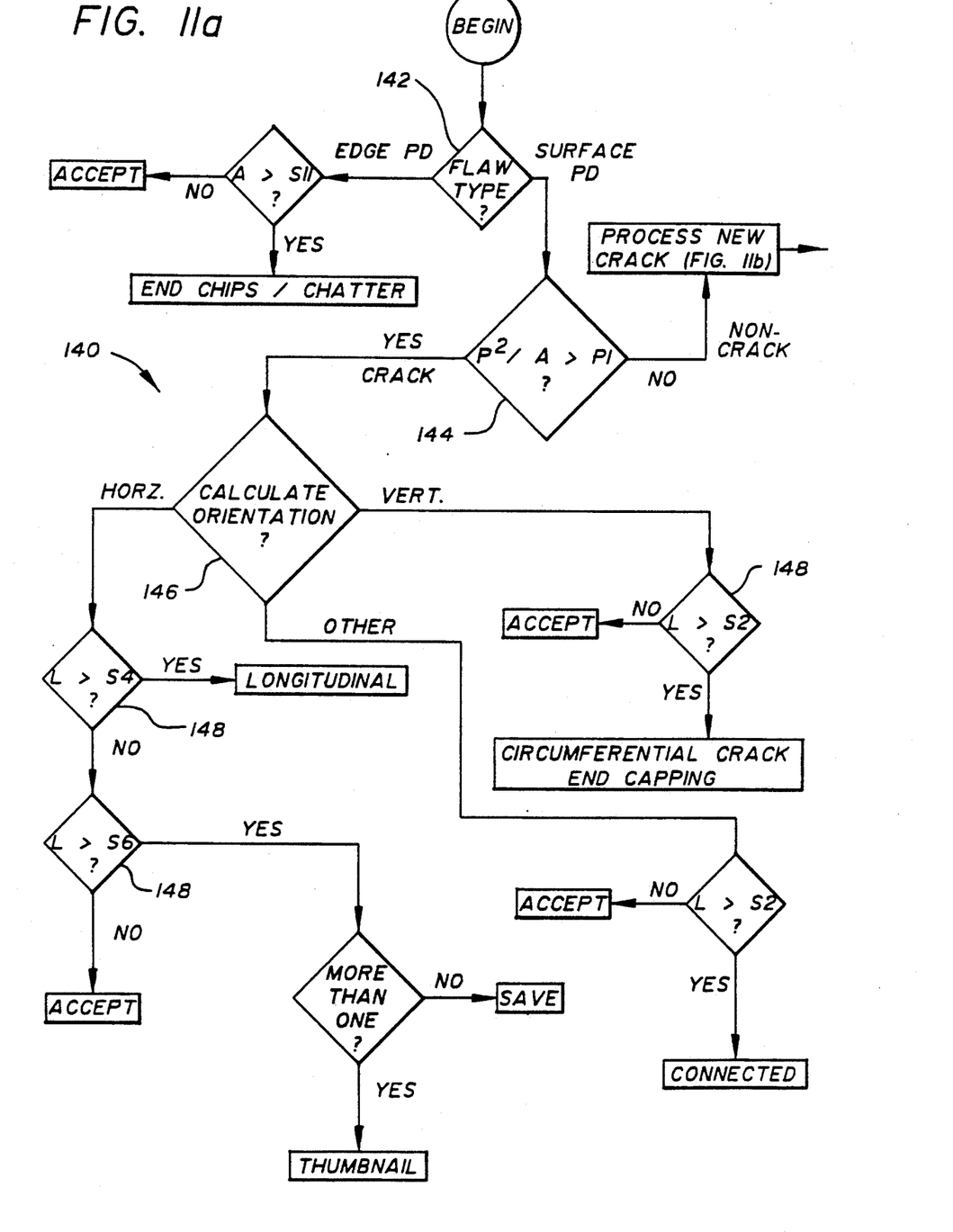
FIGS. 11a and 11b are related segments of a functional block diagram showing a decision tree used to evaluate potential pellet defects.
Figure 11B:
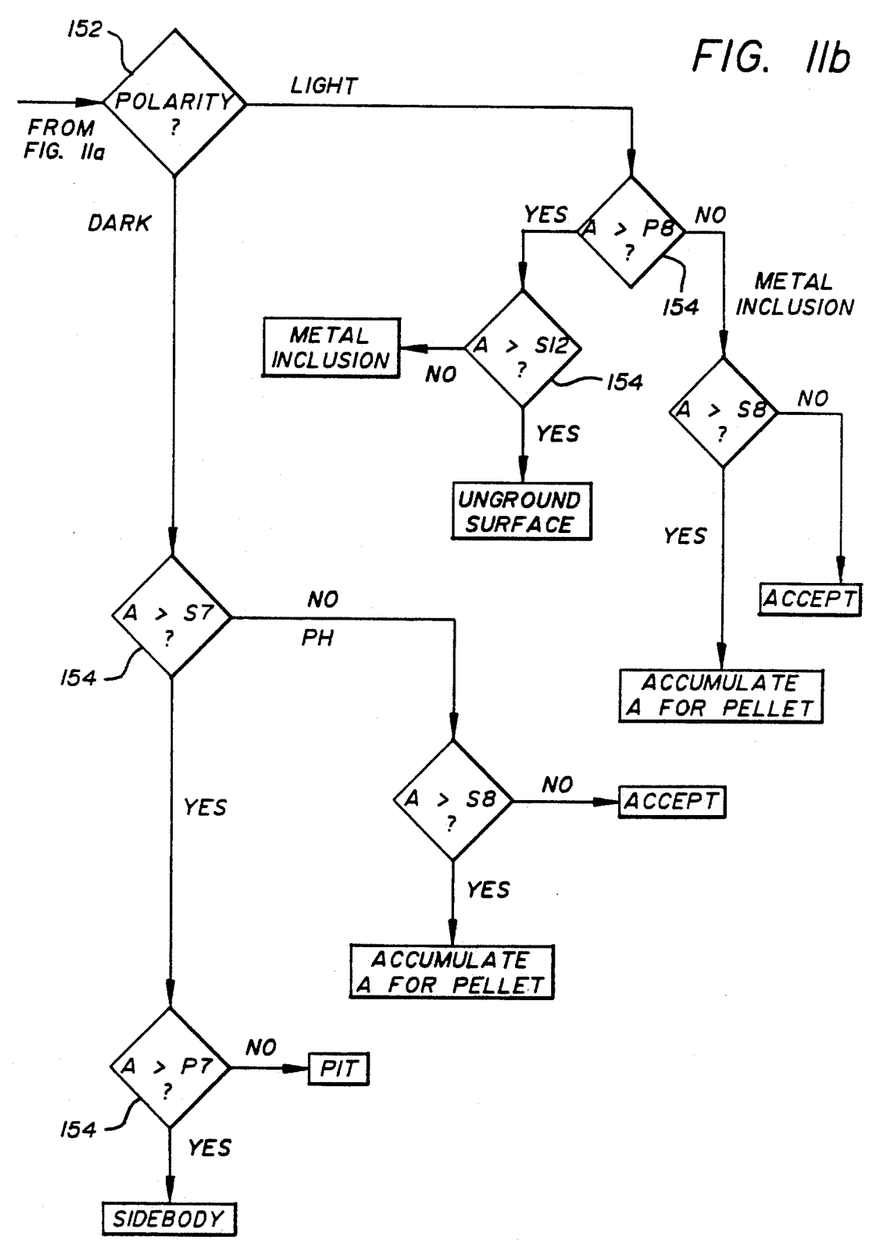

FIGS. 11a and 11b graphically illustrate a preferred decision tree 140 that is used for each potential defect or PD. A branch 142 at the flaw type is shown to distinguish between the two pipelines relating to sidebody surface PDs and edge PDs. In the sidebody defect processing procedure (FIG. 11a), a branch 144 into different legs is provided for different handling of crack and non-crack defects. For cracks, the orientation of the crack is an aspect of the blob seed parameters, and different length reject thresholds can be applied via a further branch 146 based on whether the crack is horizontal or vertical. A longitudinal, circumferential or end-cap indicating crack over a predetermined length is grounds for rejection. A single short longitudinal crack is passed, while a longer crack either generates a rejection or is stored for generating a rejection as a thumbnail crack if an additional such crack is found as well. Cracks of other orientations are acceptable unless they are longer than a predetermined threshold 148 or are related (e.g., connected) to other cracks.

TABLE I

| APA-512 GENERATED BLOB PARAMETER | DESCRIPTION |
| --- | --- |
| Area | The number of pixels in a blob |
| Perimeter | The length of the perimeter of the blob |
| $\Sigma x$ | Sum of the x coordinates of all blob pixels |
| $\Sigma y$ | Sum of the y coordinates of all blob pixels |
| $\Sigma x^2$ | Sum of the squares of the x coordinates of all blob pixels |
| $\Sigma y^2$ | Sum of the squares of the y coordinates of all blob pixels |
| $\Sigma xy$ | Sum of the products of the x and y coordinates of all blob pixels |
| Polarity | Whether the blob is foreground or background |
| Bounding Box | Minimum and maximum of the x and y coordinates of all pixels in the blob |
| Structure | Parent/Child/Sibling relationships; Number of holes in the blob; Whether or not the blob is on the boundary |

For non-crack defects (FIG. 11b), a branch 152 in the decision tree is provided for whether the defect is relatively lighter or darker, lighter defects representing metal inclusions or unground surfaces, and darker defects representing voids, pits or the like. For these defects, the rejection setpoints 154 are based on defect area. The type of defect detected, the area and the number are likewise used to distinguish good pellets from bad ones. Similarly, in the edge defect branch, a PD having an area greater than a predetermined threshold generates a rejection decision.

In addition to generating accept/reject decisions as shown in FIGS. 11a and 11b, and remembering PDs already processed for the particular pellet (for potential rejection due to their number), the system preferably logs the defects found. This is useful from a management information standpoint as it enables defects to be correlated to manufacturing parameters, pellet lots or batches, particular batches of pellet materials and the like. The selection rate can then be improved by correcting or adjusting manufacturing parameters that are identified as related to the number of particular defects.

The invention provides a very consistent and dependable method and apparatus for distinguishing among pellets using objective criteria. The subjectivity and variability of human inspection operations are avoided. Additionally, the invention eliminates significant low-level radiation exposure to human inspectors, and also eliminates the need for inspectors to lift and move heavy trays of pellets.

The invention is applicable to general automated inspection applications. Although the preferred embodiment described here is specifically intended for inspection of nuclear fuel pellets, which are small cylindrical objects, many of the same signal processing techniques and apparatus can be used in other specific surface inspection applications. All that is needed is the proper presentation of the object to be inspected to the camera and optics.

The invention having been disclosed in connection with the foregoing exemplary embodiments, variations now will occur to persons skilled in the art. Whereas the invention is not intended to be limited to the preferred embodiments disclosed as examples, reference should be made to the appended claims rather than the foregoing embodiments in order to assess the scope of the invention in which exclusive rights are claimed.

We claim:

1. A method for non-contact flaw detection for cylindrical nuclear fuel pellets, comprising the steps of:
   transporting a succession of the pellets substantially continuously along a path while rotating the pellets about a longitudinal axis of the pellets and advancing the pellets along the longitudinal axis;
   illuminating the workpieces at an inspection area;
   recording a plurality of line scans for at least a subset of the pellets and digitizing the line scans to define a pixel data image having successive lines in which individual pixels are displaced by an offset from adjacent pixels on the pellets recorded in next and previous said line scans, the offset corresponding to an extent of said rotating and advancing;
   processing values of pixels in the image to define an average value, a high threshold and a low threshold, the high and low thresholds being within a predetermined range of the average value, and comparing the values of the pixels to said high and low thresholds to generate an image map of pixels as a result of said comparing;
   associating pixels in the binary image map to cancel said offset;
   applying at least one convolution matrix to a region of interest in the image map, the convolution matrix having a two-dimensional series of factors applied to each pixel in the region of interest for generating a resulting pixel matrix, said factors being chosen for at least one of deemphasizing isolated pixels falling outside the thresholds and enhancing contrast along the edge of the pellets;
   determining at least one of parameters including a total number of pixels outside the thresholds, and at least one dimension of a blob of neighboring pixels outside the thresholds;
   locating in the pixels in the binary image map, as associated to cancel said offset, pixels at an edge of the pellets;
   matching the pixels in the binary image map with a nominal contour for the edge of the pellets; and,
   selecting and rejecting the workpieces as a function of said parameters and said matching of the pixels to the nominal contour.

2. The method according to claim 1, wherein said processing comprises applying a video finite impulse response filter to the values of the pixels to reduce noise present in the pixel data image.

3. The method according to claim 2, wherein said processing is accomplished on a region of interest corresponding to a region of associated pixels that contains an image of a workpiece.

4. The method according to claim 1, wherein said at least one convolution matrix includes a matrix of factors representing an edge, includes applying for enhancing in the resulting pixel matrix a contrast at the edge of the pellets, and further comprising defining a nominal edge of the pellets from a best fit with the edge as thereby enhanced, and counting and associating pellet edge pixels falling outside the thresholds and displaced from the nominal edge, for assessing conformity of the pellet edge pixels to the nominal edge.

5. The method according to claim 1, wherein said recording includes storing the image map in an image buffer and the processing comprises counting and associating steps for assessing surface flaws, and matching a best fit of a contrasting edge in the pixel image to a nominal edge; for assessing edge flaws, and wherein said assessing of surface flaws and edge flaws, respectively, are accomplished simultaneously along at least two data paths of the pixel data image.

6. The method according to claim 1, wherein said recording includes obtaining at least two pixel data images representing one of abutting sections from at least one of adjacent areas and adjacent edge sections of an individual pellet, and further comprising associating the at least two tiles of pixels representing the abutting sections, and wherein said counting and associating includes discriminating for blobs in said at least two tiles which bridge across a boundary between the tiles.

7. The method according to claim 1, wherein the recording is accomplished using a line scanning camera having a plurality of sensor elements, and further comprising recording at least one of an offset value and a gain value for each of the sensor elements, and normalizing output levels from the sensor elements to cancel variations in said at least one of the offset value and the gain value among the sensor elements.

8. A flaw detection apparatus for detecting surface and edge flaws on substantially cylindrical nuclear fuel pellets, comprising:
   a transport mechanism operable to rotate and axially advance the pellets along a transport path;
   illumination means and a line scan camera, operable to develop a succession of line scan signals representing reflectivity of the pellets passing a viewing area;

means for digitizing the line scan signals to acquire and store in an image buffer a pixel data image for the pellets;

an image data filter comprising at least one of an averaging means, a video finite impulse response filter and a convolution mask processor, operable to process the pixel data for generating a pixel map representing variations in reflectivity of individual said pellets beyond at least one threshold limit;

a processor operable to analyze the pixel map for identifying grouped blobs of pixels beyond the threshold limit and to count at least one of said blobs and said pixels beyond the threshold limit, for assessing quality of the pellet; and, wherein the image data filter and the processor define two parallel image processing pipelines operating on the pixel map simultaneously, the two parallel image processing pipelines being operable for detecting and assessing side flaws and edge flaws, respectively.

9. The flaw detection apparatus according to claim 8, wherein the image data filter is operable to average values of pixels at least within a region of interest and to generate upper and lower thresholds based on the average, said pixel map distinguishing between pixels between the thresholds and pixels outside the thresholds.

10. The flaw detection apparatus according to claim 9, wherein the average is based at least partly on an output of the video finite impulse response filter.

11. The flaw detection apparatus according to claim 8, wherein the line scan camera includes a plurality of sensor elements, and further comprising means for setting at least one of an offset value and a gain value for each of the sensor element, at least one of the means for digitizing, the image data filter and the processor being operable to normalize values generated from the sensor elements to cancel variations in said at least one of offset and gain.

12. A flaw detection apparatus for nuclear fuel pellets, comprising:

a transport mechanism operable to rotate and axially advance the pellets along a transport path;

illumination means and a line scan camera, operable to develop a succession of line scan signals representing reflectivity of the pellets passing a viewing area;

means for digitizing the line scan signals to acquire and store in an image buffer a pixel data image for the pellets;

an image data filter comprising at least one of an averaging means, a video finite impulse response filter and a convolution mask processor, operable to process the pixel data for generating a pixel map representing variations in reflectivity of individual said pellets beyond at least one threshold limit;

a processor operable to analyze the pixel map for identifying grouped blobs of pixels beyond the threshold limit and to count at least one of said blobs and said pixels beyond the threshold limit, for assessing quality of the pellet; and, wherein the image data filter and the processor define two substantially parallel image processing pipelines for detecting and assessing side flaws and edge flaws, respectively, and wherein the image data filter is operable to enhance contrast of an edge of the pellet by application of a convolution mask representing a variation among a group of adjacent pixels characteristic of the edge, the processor being operable to define and count blobs composed of pixels detected along an extreme edge of the pellet that are displaced from a nominal line that best fits the extreme edge.

13. The flaw detection apparatus according to claim 12, wherein the processor is operable to make an accept/reject decision for each pellet based on a count of the blobs, a count of the pixels outside the threshold, at least one dimension of the blobs, and the count of pixels along the extreme edge that are displaced.

* * * * *